United States Patent [19]

Hsu et al.

[11] Patent Number: 4,519,948
[45] Date of Patent: May 28, 1985

[54] PROCESS FOR OXIDIZING A PHENOL TO A P-BENZOQUINONE

[75] Inventors: Chao-Yang Hsu, Media; James E. Lyons, Wallingford, both of Pa.

[73] Assignee: Sun Tech, Inc., Philadelphia, Pa.

[21] Appl. No.: 527,891

[22] Filed: Aug. 30, 1983

Related U.S. Application Data

[63] Continuation-in-part of Ser. No. 423,985, Sep. 27, 1982, abandoned.

[51] Int. Cl.$^3$ .................. C07C 45/16; C07C 49/64
[52] U.S. Cl. ................................................. 260/396 R
[58] Field of Search .................................... 260/396 R

[56] References Cited

U.S. PATENT DOCUMENTS

| | | | |
|---|---|---|---|
| 3,870,731 | 3/1975 | Hutchings | 260/396 R |
| 3,987,068 | 10/1976 | Reilly | 260/396 R |
| 4,208,339 | 6/1980 | Costantini et al. | 260/396 R |

FOREIGN PATENT DOCUMENTS 420022  9/1980  European Pat. Off. ........ 260/396 R

*Primary Examiner*—Glennon H. Hollrah
*Assistant Examiner*—Raymond Covington
*Attorney, Agent, or Firm*—J. Edward Hess; Donald R. Johnson; Stanford M. Back

[57] ABSTRACT

Phenol or a substituted phenol is oxidized to the corresponding benzoquinone or substituted benzoquinone in a nitroalkane solvent in the presence of a copper ion catalyst promoted with a base selected from alkali metal phenoxides, and secondary or tertiary lower alkyl amines.

8 Claims, No Drawings

PROCESS FOR OXIDIZING A PHENOL TO A P-BENZOQUINONE

This application is a continuation-in-part of application Ser. No. 423,985 filed Sept. 27, 1982 now abandoned.

BACKGROUND OF THE INVENTION

It is known in the art to oxidize phenol to p-benzoquinone with oxygen in the presence of a copper ion catalyst and such a process is disclosed in U.S. Pat. No. 3,987,068. In that patent the oxidation is carried out in a nitrile solvent using a complex formed from the copper catalyst and the solvent, and the operating conditions are said to be a temperature of from about 0° to 100° C. and a partial pressure of oxygen of from about 7 to 200 (preferably 14 to 100) atmospheres. As pointed out in U.S. Pat. No. 3,987,068, yield of quinone product increase with increased partial pressure of oxygen and it appears from the data therein that partial pressures of oxygen above about 100 atmospheres are required in order to achieve conversions of phenol to p-benzoquinone on the order of about 75%. Such oxygen pressures are too high to be useful in an economical commercial process because they require special equipment of high capital cost.

U.S. Pat. No. 3,870,731 relates to the oxidation of phenols to benzoquinones in the presence of copper salts as catalysts where an anionic liquid of the catalyst such as thiocyanate, cyanate, cyanide and halogen ions improve catalyst activity. In such reactions a solvent such as water is disclosed and other polar solvents soluble or miscible with water may be used. Such solvents are exemplified by certain amides, alcohols, and sulfoxides. It is also stated that any of the various solvents may be used alone or in combination with water in any desired ratio.

In our U.S. patent application Ser. No. 284,893 filed July 20, 1981 now abandoned and its continuation application Ser. No. 423,984 filed Sept. 27, 1982 now abandoned, we disclose that the copper catalyzed oxidation of a phenol to a p-benzoquinone can be significantly improved by carrying out the reaction in a nitrile solvent and using a divalent copper catalyst promoted with a alkali metal base wherein the molar ratio of base to copper catalyst is no greater than 2.0. Use of about 10% by volume or less of water in the reaction system gives further improvement to the reaction in that selectivity is increased.

In our U.S. patent application Ser. No. 339,965 filed Jan. 18, 1982 we disclose that a copper catalyzed process for oxidation of a phenol to a p-benzoquinone can be significantly improved so as to enable operation at lower, commercially useful pressures and while also achieving an improved selectivity to product, by conducting the oxidation of phenol in the presence of a monovalent copper ion catalyst (e.g. $Cu^+$) in a conventional solvent system, preferably a nitrile solvent, which is modified with water.

SUMMARY OF THE INVENTION

Another technique has now been found to improve the copper catalyzed process for oxidation of a phenol to p-benzoquinone or a substituted benzoquinone so as to enable operation at increased rate of reaction and selectivity to product. In accord with this invention, such objectives are achieved by conducting the oxidation of a phenol in a nitroalkane as a solvent and in the presence of a copper ion catalyst which is promoted with a base selected from alkali metal phenoxides and secondary or tertiary lower alkyl amines.

According to the invention, phenol and substituted phenols are converted to corresponding p-benzoquinone and substituted p-benzoquinones as illustrated in the following reaction:

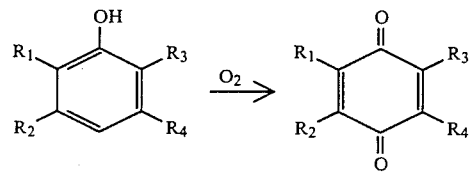

wherein $R_1$, $R_2$, $R_3$ and $R_4$ may be the same or different and may comprise hydrogen, halo or cyano, alkyl or alkoxy containing 1 to about 12 carbon atoms; phenyl, naphthyl, phenylalkyl, alkylphenyl, phenoxy or phenalkoxy, containing 7 to about 16 carbon atoms; and $R_1$ and $R_2$ or $R_3$ and $R_4$ may be joined to form an aliphatic, aryl or hetero ring. Specific R groups include chloro, cyano, methyl, ethyl, propyl, butyl, isobutyl, tert-butyl, pentyl, p-tolyl, p-anisyl, methoxy, t-butoxy, phenoxy, p-methylphenoxy, and the like. Preferred phenols useful in the process are phenol, o-chlorophenol, o-cresol, m-cresol, 2,5-and 2,6-di-t-butylphenol, 2-t-butylphenol, 2,6-dimethylphenol, and 1-naphthol. When $R_1$ and $R_2$ or $R_3$ and $R_4$ joined, the resulting p-benzoquinones will be those derived from naphthalene, quinoline, isoquinoline, chroman (dihydrobenzopyran), indole and the like.

In carrying out the process of the invention, conventional temperature conditions and a monovalent or divalent copper catalyst may be used. Thus, a temperature of from about 20° to about 100° C. (preferably about 50° to 75° C.) will be employed. The copper catalyst will preferably be a copper halide, preferably chloride, although nitrate is operable and mixtures of such salts also may be used. The mole ratio of catalyst to phenol reactant may very widely, on the order of from about 50:1 to 1:1, preferably about 15:1 to 5:1. The base promoter will be selected from the group of alkali metal phenoxides (e.g. sodium, potassium, lithium and cesium phenoxides) and secondary or tertiary lower alkyl amines (e.g. $C_1$ to $C_4$ alkyl amines) such as dimethylamine, diethylamine (DEA), dibutylamine, trimethylamine, tripropylamine, triethylamine (TEA) and the like. The amount of promoter is not critical. Suitable amounts are from about 0.1 to about 1.9 mole promoter per mole of catalyst, preferably about 1:1. As indicated above, the reaction can be carried out at moderate pressures, generally between about 100 and about 500 psig partial pressure of oxygen, preferably between about 200 and 400 psig. Mixtures of oxygen and nitrogen, air alone, or oxygen alone may be used, but preferably mixtures of oxygen and nitrogen such as air will be employed as the oxygenating medium.

As indicated, the solvent used in the process may be a $C_1$ to $C_6$ nitroalkane (preferably $C_1$ to $C_3$) such as nitromethane, nitroethane and the nitropropane isomers. Nitromethane is the preferred solvent.

In order to further illustrate the invention, the following examples are given:

EXAMPLE 1

A solution of 16 mmole of phenol in 5 ml. of nitromethane containing 0.55 mmole of catalyst and 0.55 mmole of the base was agitated in a magnetically stirred mini-antoclave under an initial total pressure of 750 psig and was oxidized over a three-hour period with a mixture of 40% (vol.) oxygen and 60% nitrogen. The reaction parameters and results obtained are shown in the following Table I. Substantially improved conversions and/or selectivities were achieved.

TABLE 1
EFFECT OF BASES ON THE RATE AND SELECTIVITY OF THE COPPER CATALYZED OXIDATION OF PHENOL

| RUN | CATALYST | BASE | SOLVENT | CONV. (%) | SELECTIVITY (%) |
|---|---|---|---|---|---|
| 1 | $CuCl_2$ | — | $CH_3NO_2$ | 28 | 43 |
| 2 | $CuCl_2$ | LiOPh | $CH_3NO_2$ | 31 | 62 |
| 3 | $CuCl_2$ | TEA | $CH_3NO_2$ | 82 | 43 |
| 4 | $CuCl_2$ | DEA | $CH_3NO_2$ | 60 | 35 |
| 5 | CuCl | — | $CH_3NO_2$ | 17 | 28 |
| 6 | CuCl | LiOPh | $CH_3NO_2$ | 42 | 56 |
| 7 | CuCl | TEA | $CH_3NO_2$ | 57 | 40 |
| 8 | CuCl | DEA | $CH_3NO_2$ | 62 | 35 |

EXAMPLES 2–7

In experiments which may be conducted substantially as described in example 1, except for substitution of the substituted phenols listed below, good improvements in selectivity to the corresponding substituted benzoquinones, conversion and/or yield are achieved:

TABLE II

| Ex. No | Substituted phenol | Product |
|---|---|---|
| 2 | o-cresol | 2-methyl-p-benzoquinone |
| 3 | m-cresol | 2-methyl-p-benzoquinone |
| 4 | 2,6-dimethylphenol | 2,6-dimethyl-p-benzoquinone |
| 5 | 2,6-di-t-butylphenol | 2,6-di-tert-butyl-p-benzoquinone |
| 6 | o-t-butylphenol | 2-tert-butyl-p-benzoquinone |
| 7 | 2,5-di-t-butylphenol | 2,5-di-tert-butyl-p-benzoquinone |

We claim:

1. In the process of oxidizing phenol or a substituted phenol of the formula

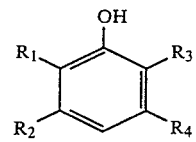

wherein $R_1$, $R_2$, $R_3$, and $R_4$ may be the same or different, and are selected from the group consisting of hydrogen, halo, cyano, $C_1$–$C_{12}$ alkyl, $C_1$–$C_{12}$ alkoxy, phenyl, naphthyl, phenylalky, alkylphenyl, $C_7$–$C_{16}$ phenoxy, or $C_7$–$C_{16}$ phenalkoxy; and $R_1$ and $R_2$, or $R_3$ and $R_4$ may be joined to form an aliphatic, aryl, or hetero ring selected from the group consisting of naphthalene, quinoline, isoquinoline, chroman, and indole, to benzoquinone or a substituted benzoquinone of the formula

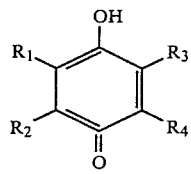

where $R_1$, $R_2$, $R_3$, and $R_4$ are as defined above, with a copper salt catalyst selected from the group of halides and nitrates, the improvement which comprises carrying out the reaction in a $C_1$ to $C_6$ nitroalkane as solvent and promoting the catalyst with a base selected from alkali metal phenoxides, and secondary or tertiary lower alkyl amines.

2. The process of claim 1 wherein the solvent is nitromethane.

3. The process of claim 2 wherein the promoter is lithium phenoxide.

4. The process of claim 1 wherein the phenol is an alkylphenol.

5. The process of claim 4 wherein the alkylphenol is o-cresol or m-cresol.

6. The process of claim 4 wherein the alkylphenol is di-methylphenol.

7. The process of claim 4 wherein the alkylphenol is a di-tert-butylphenol.

8. The process of claim 4 wherein the alkylphenol is o-t-butylphenol.

* * * * *